United States Patent [19]

Eigen et al.

[11] 4,407,789
[45] Oct. 4, 1983

[54] GROUND RICE HULLS IN BODY POWDERS

[75] Inventors: Edward Eigen, East Brunswick; Dina I. Brachman, Highland Park; Stuart D. Friedman, Bound Brook, all of N.J.

[73] Assignee: Colgate-Palmolive Company, New York, N.Y.

[21] Appl. No.: 321,874

[22] Filed: Nov. 16, 1981

[51] Int. Cl.³ .................. A61K 7/46; A61K 7/021; A61K 7/32; A61K 7/035
[52] U.S. Cl. .................. 424/69; 252/522 R; 424/63; 424/65; 424/358
[58] Field of Search .............. 424/69, 63, 65, 69; 252/522

[56] References Cited

U.S. PATENT DOCUMENTS

| 415,351 | 11/1889 | Quaglio | 424/69 |
| 1,968,475 | 7/1934 | Beckwith et al. | 424/69 |
| 1,995,663 | 3/1935 | Bollmann et al. | 424/69 |
| 2,016,289 | 10/1935 | McGill | 252/167 |

FOREIGN PATENT DOCUMENTS 1141994 2/1969 United Kingdom .................. 424/69

OTHER PUBLICATIONS

Chem. Abs., vol. 22, 11/1928, p. 4665, Scurti.
Chem. Abs., vol. 22, 6/1928, p. 2415, Borasio.
Martindale, The Extra Pharmacopoeia, 1943, 22nd Ed., vol. II, p. 738.

Primary Examiner—Dale R. Ore
Attorney, Agent, or Firm—Herbert S. Sylvester; Murray M. Grill; John A. Stemwedel

[57] ABSTRACT

Novel high absorption body powder compositions comprising rice hulls ground to a particle fineness such that the material passes through a 200 mesh sieve, and preferably passes through a 325 mesh sieve, as the basic and main powder constituent.

11 Claims, No Drawings

GROUND RICE HULLS IN BODY POWDERS

This invention relates to high moisture absorbent body powder compositions having good texture and feel properties comprising around rice hulls of a size which pass a 200 mesh sieve as the base powder.

BACKGROUND AND PRIOR ART

Rice hulls, a byproduct in the preparation of rice grains, has found many uses. One particular use is as a cleaning scouring abrasive in mechanics' handsoaps, wherein the rice hulls are ground to pass 20 mesh but not 100 mesh, in amounts of 10-25% by weight of the soap composition, as disclosed in chapter 12 page 331 of *Rice Chemistry and Technology*, Edited by D. F Houston, published by American Association of Cereal Chemists, Inc., St. Paul, Minnesota, 1972. Another use for finely ground hulls, described on page 332 of the same book, is as a filler in plastics and plywood glues. Still another use is as a carrier or adsorbent for materials ranging from vitamins to pesticides to explosives. However, there is no disclosure of the use of finely ground rice hulls as a powder base for body powders.

Talc, a natural hydrous magnesium silicate, is the major ingredient used today in body powders. However, talc has low water absorption properties and has been found irritating to the tender skins of babies. Accordingly, corn or rice starch has been substituted for talc as a dusting powder as shown in U.S. Pat. No. 2,469,957. *Handbook of Cosmetic Materials*, by Leon A. Greenberg and David Lester (1954) pages 303 and 304 also describes the starches including rice starch and their uses in dusting powders and face powders, as well as their possible adverse dermatological reactions. The use of rice starch in bath powders and face powders, as well as possible problems encountered therewith, is also disclosed in *Cosmetics Science and Technology*, Second edition, Vol. 2, edited by M. S. Balsam and Edward Sagarin (1957), pages 515 and 339. *Riechstoffe Seifen Kosmetika* by H. Janistyn, Vol. 1 (1950) page 372 also discloses rice starch which is obtained from fragmented rice, as a raw material for cosmetics. Starches generally, and rice starch specifically, as a constituent of face powder is disclosed in *The Chemistry and Manufacture of Cosmetics* by Maison G. de Navarre, (1981) page 337. Thus, it is apparent from the prior art that rice starch has been substituted for part or all of the talc in a body powder composition in order to eliminate some of the deficiencies of talc. However, additional problems have arisen from the use of starches as aforedescribed, and the major deficiency of insufficient moisture absorbency of said powders is still existent.

The prior art also discloses face powders containing small amounts of a special fraction of dehulled oat groats ground to 60-70 mesh, in U.S. Pat. No. 2,436,818; and face powders containing large amounts of walnut shell flour as filler, in U.S. Pat. No. 4,279,890.

Although the prior art discloses rice starch which is an extract from rice grains, and dehulled oat grains, and walnut shell flour as an ingredient in body powders, there is no disclosure of rice hulls, a byproduct in the preparation of rice grains. More specifically, rice grains are obtained by first dehulling and then debranning the rice product. Finely ground rice hulls as the powder base for high absorption body powder is the subject matter of this invention.

SUMMARY OF THE INVENTION

The primary object of this invention is to provide a body powder composition of high absorbency comprising finely divided rice hulls ground to a fineness such that the material passes through a 200 mesh sieve as the base powder. All references to sieve sizes herein refer to the U.S. sieve series.

Another object of this invention is to provide a body powder composition of suitable texture and feel, containing up to 98% ground rice hulls which pass through a 200 mesh sieve.

Another object of this invention is to provide a naturally flesh colored body powder comprising finely divided rice hulls as the base powder.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects and in accordance with the present invention, as embodied and broadly described herein, the highly absorbent body powder composition of this invention comprises finely ground rice hulls which pass through a 200 mesh sieve as the base powder.

More specifically, present invention relates to a high absorbent body powder composition having good texture and feel properties comprising up to 98% by weight of ground rice hulls which pass through a 200 mesh sieve as the powder base. Talc may be substituted for part of the ground rice hulls provided the properties of this composition are not adversely affected.

It has been unexpectedly found that ground rice hulls which pass through a 200 mesh sieve can be effectively used as a substitute for talc in a body powder with the feel and texture of talc, but with a greater capacity to absorb moisture and sweat secretions. Dried ground rice hulls absorbs moisture (16%), while talc absorbs very little (0.5%). The fluid absorbency is determined by placing a weighed amount of a dry sample of rice hulls or talc in a 90% humidity chamber until a constant weight is reached, and reweighing the fluid saturated sample, the difference in weight constituting the % absorbency. The natural flesh color of said ground rice hulls makes it particularly attractive as a powder base for face powders as well as dusting powders since it readily blends with the skin tone. Talc, on the other hand, leaves a white layer of powder unless pigmented. The ground rice hulls is an asbestos-free natural product and considerably less costly than talc, making it a very attractive substitute for talc in body powders. Extracts of rice hulls have been reported as having antimicrobial activity in *Cereal Food World* January 1981, Vol. 26, No. 1, pages 19-25, thereby providing still another advantage in the use of ground rice hulls as the powder base in body powders. This inherent antimicrobial activity may provide disinfectant properties and make ground rice hulls potentially useful as a deodorant powder. All of these attributes makes ground rice hulls an excellent substitute for talc or starch in body powder compositions.

It is essential that the rice hulls be ground to a particle size so that all particles pass through a 200 mesh sieve (less than 74μ), and preferably all particles pass through a 270 mesh sieve (less than 53μ) and most preferably all particles pass through a 325 mesh sieve (less than 44μ). The particle size distribution is most preferably about 2 to 40μ with an average median size of about 11.5 to 19μ. Particles which are returned on a 200 mesh sieve are not useful as a powder base because they impart a gritty feel and texture to the body powder. The rice hulls are usually ground for about 48 hours in ball mills and sieved for about 3 hours. However, other suitable means and devices known in the art of grinding the rice hulls can also be utilized provided the particles pass through a 200 mesh sieve screen.

The proportion of ground rice hulls when used as the sole base powder may be as high as 98% by weight of the body powder composition. Amounts usually used are about 50% to 98% by weight. However, other conventional powders such as talc or starch may be substituted for part of the ground rice hull powder in amounts of less than 50% of the total base powder content.

The present body powder compositions containing ground rice hulls have all the attributes of a bath dusting powder, namely, spreads on easily, rubs in easily, absorbs on the skin readily, disappears on the skin quickly, skin feels smooth and soft after application, it's not sticky and has good texture. In summation, the composition functions efficiently as a body powder. It supplies a lubricant which will absorb moisture and facilitate dressing.

Instant body powder compositions may also be used as a face powder, both in loose or compacted form, suitably tinted with pigments such as zinc oxide, titanium dioxide, the iron oxides, and the D & C Red, Yellow and Orange colors, and mixtures thereof.

Another essential ingredient in instant body powder compositions is a binding agent for the powdered rice hulls which is preferably a metallic stearate such as zinc, aluminum or magnesium stearate, in amounts not to exceed 15% and preferably about 1-5% by weight for loose powders and about 5-15% for pressed or compacted powders. The presence of the stearate improves slip and flow properties of the product. However, minor amounts of other binders or mixtures of binders may be used such as lanolin, mineral oil, pressed stearic acid, etc., particularly in the formulation of a compacted face powder.

Minor amounts of optional ingredients may be added to the body powder compositions of present invention, including a fragrance or perfume oil; preservatives; magnesium carbonate or kaolin which absorbs and distributes the perfume oil in the powdered product and generally functions as a perfume carrier. Tricalcium phosphate may be added to provide anticaking properties and aid in the flow properties of the product.

Density modifiers such as zinc oxide and calcium carbonate to increase density, and Cabosil (fumed silica) or magnesium carbonate to decrease density may also be added. Similarly, opacifiers and pigments such as titanium dioxide, iron oxide may be added, especially in face powders. Emollients such as isopropyl myristate and other fatty acid esters may be added to formulate an emollient bath powder. The amount of each additive should not exceed about 15% by weight and preferably constitutes about 0.1-15% by weight of the total composition.

Germicidal or antiseptic compounds may be added to present body powder compositions such as quaternary ammonium salts, boric acid, salicylic acid, ichthammol and other germicidal and antiseptic agents may be added in minor amounts, preferably not to exceed 5% by weight of the composition.

The high absorption body powder of the present invention is generally prepared by intimately mixing the finely ground rice hulls with the other dry ingredients until a homogeneous powdered mixture is obtained. The perfume oil may be premixed with the magnesium carbonate prior to its admixture with the ground rice hulls.

The body powder compositions of present invention include bath powder, foot powder, face powder, both loose and compacted, and loose or compacted deodorant and/or perfume powder products.

DETAILED DESCRIPTION OF THE INVENTION

The following examples are given to illustrate this invention further. However, the examples should not be construed as limiting the invention. Many variations are possible without departing from the scope of this invention. In this application all proportions are by weight unless otherwise indicated.

EXAMPLE 1

| Dusting Powder | |
|---|---|
| Ingredient | % |
| Ground Rice Hulls (particles pass a 325 mesh sieve) | 97.6 |
| Zinc stearate | 1.0 |
| Magnesium carbonate | 1.0 |
| Perfume | 0.4 |

The perfume is premixed with the magnesium carbonate, which is then dry mixed with the ground rice hulls and the zinc stearate.

The resultant high absorbent powder, which is flesh colored (tan) has a good feel and texture.

EXAMPLE 2

| Dusting Powder | |
|---|---|
| Ingredient | % |
| Ground Rice Hulls (particles pass a 325 mesh sieve) | 96.1 |
| Magnesium carbonate | 1.0 |
| Perfume | 0.3 |
| Preservative | 0.1 |
| Zinc stearate | 1.0 |
| Tricalcium phosphate | 1.5 |

This high absorbent product has an apparent density of 0.43 g/cc which is lighter than the apparent density of ground rice hulls alone (0.45 g/cc), has good texture and feel.

EXAMPLE 3

| Loose Face Powder | |
|---|---|
| Ingredient | % |
| Ground Rice Hulls (particles pass a 325 mesh sieve) | 54.55 |
| Zinc stearate | 5.00 |
| Zinc oxide | 15.00 |
| Magnesium carbonate | 5.00 |
| 33⅓% Perfume in magnesium carbonate powder | 7.5 |
| 20% iron oxide in talc | 12.5 |
| 20% D & C Red in talc | 0.05 |
| 20% D & C Yellow in talc | 0.40 |

A brunette face powder is produced by dry mixing the above ingredients. The resulting face powder has a good texture and feel.

EXAMPLE 4

| Loose Face Powder | |
|---|---|
| Ingredient | % |
| Ground Rice Hulls (particles pass a 325 mesh sieve) | 65.63 |
| Zinc stearate | 5.00 |
| Zinc oxide | 15.00 |
| Magnesium carbonate | 5.00 |
| 33⅓% perfume in magnesium carbonate | 7.5 |
| 20% D & C Red in talc | 0.07 |
| 20% D & C Orange in talc | 1.0 |
| 20% D & C Yellow in talc | 0.8 |

A lighter colored face powder, than in Example 3, is produced by dry mixing which has similarly good texture and feel.

The color can be further changed by the addition of various colored iron oxides and changing the percentages of the various coloring ingredients.

EXAMPLE 5

| Pressed Face Powder | |
|---|---|
| Ingredient | % |
| Ground Rice Hulls (particles pass a 325 mesh sieve) | 58.15 |
| Titanium dioxide | 3.75 |
| Zinc stearate | 7.5 |
| Zinc oxide | 0.2 |
| Calcium carbonate | 7.5 |
| 20% iron oxide in talc | 17.4 |
| Perfume | 0.5 |
| Pressed Face Powder Binder[1] | 5.0 |

[1] 25.868% in lanolin
59.477% mineral oil
10.424% pressed stearic acid
3.861% cetyl alcohol
0.370% preservative The ingredients are thoroughly mixed and then compressed into a container. The resultant compact face powder spreads on easily, is not sticky, has good texture and feel.

EXAMPLE 6

| Pressed Face Powder | |
|---|---|
| Ingredient | % |
| Ground Rice Hulls (particles pass a 325 mesh sieve) | 74.875 |
| Titanium dioxide | 3.75 |
| Zinc stearate | 7.50 |
| Zinc oxide | 0.2 |
| Calcium carbonate | 7.5 |
| 20% iron oxide in talc | 0.025 |
| 20% D & C Red in talc | 0.25 |
| 20% D & C Orange in talc | 0.15 |

-continued

| Pressed Face Powder | |
|---|---|
| Ingredient | % |
| 20% D & C Yellow in talc | 0.25 |
| Perfume | 0.5 |
| Pressed Face Powder Binder | 5.0 |

The ingredients are thoroughly mixed and compressed into a container. This product is lighter in color than that of Example 5, and also spreads on easily, is not sticky, has good feel and texture.

Other ingredients may be added to the above examples to modify the final product, such as density modifiers to produce heavy or light body powders. Colors or pigments may be added to change the color of the finished product. Other stearates may be substituted for the zinc stearate in the above examples.

It is understood that the foregoing detailed description is given merely by way of illustration and that variations may be made therein without departing from the spirit of the invention. The Abstract above is merely for the convenience of technical searchers and is not to be given any weight with respect to the scope of the invention.

We claim:

1. A highly absorbent body powder composition consisting essentially of finely ground rice hulls which pass through a 200 mesh sieve as the base powder, in amounts up to 98% by weight of the composition and from 1 up to 15% by weight of the total composition of a suitable binding agent.

2. A body powder composition according to claim 1, wherein the ground rice hull particles pass through a 325 mesh sieve.

3. A body powder composition according to claim 1, containing talc in an amount less than 50% of the ground rice hull content.

4. A body powder composition according to claim 1, wherein the ground rice hulls is the sole base powder in an amount of about 50% to 98% by weight of the composition.

5. A body powder according to claim 1, wherein the binding agent is a metallic stearate and is present in an amount from about 1-15% by weight.

6. A body powder according to claim 5, wherein the binding agent is selected from the group consisting of zinc, magnesium and aluminum stearate.

7. A body powder according to claim 6, containing about 0.1-15% by weight of a perfume and a perfume carrier.

8. A body powder according to claim 7, wherein the perfume carrier is magnesium carbonate.

9. A body powder according to claim 8, which is in the form of a dusting powder.

10. A body powder according to claim 5, which is in the form of a loose face powder.

11. A body powder according to claim 5, which is in the form of a pressed face powder.

* * * * *